US011219757B2

(12) United States Patent
Burr

(10) Patent No.: US 11,219,757 B2
(45) Date of Patent: Jan. 11, 2022

(54) ISCHEMIC TRAINING APPARATUS AND METHOD

(71) Applicant: University of Guelph, Guelph (CA)

(72) Inventor: Jamie Francis Burr, Stratford (CA)

(73) Assignee: University of Guelph, Guelph (CA)

( * ) Notice: Subject to any disclaimer, the term of this patent is extended or adjusted under 35 U.S.C. 154(b) by 1014 days.

(21) Appl. No.: 15/027,948

(22) PCT Filed: Oct. 8, 2014

(86) PCT No.: PCT/CA2014/050973
§ 371 (c)(1),
(2) Date: Apr. 7, 2016

(87) PCT Pub. No.: WO2015/051457
PCT Pub. Date: Apr. 16, 2015

(65) Prior Publication Data
US 2016/0235965 A1    Aug. 18, 2016

Related U.S. Application Data

(60) Provisional application No. 61/888,279, filed on Oct. 8, 2013.

(51) Int. Cl.
*A61N 1/04* (2006.01)
*A61B 5/022* (2006.01)
(Continued)

(52) U.S. Cl.
CPC ............ *A61N 1/0452* (2013.01); *A61B 5/022* (2013.01); *A61B 5/14551* (2013.01);
(Continued)

(58) Field of Classification Search
CPC ........ A61H 9/00; A61H 9/0007; A61H 9/005; A61H 9/0078; A61H 9/0092;
(Continued)

(56) References Cited

U.S. PATENT DOCUMENTS 5,674,262 A * 10/1997 Tumey ................. A61H 9/0078
607/48
7,207,959 B1 * 4/2007 Chandran ............ A61H 9/0078
601/149
(Continued)

FOREIGN PATENT DOCUMENTS

CA          2926377 A1    4/2015
WO    WO 2013/025481 A1    2/2013
(Continued)

OTHER PUBLICATIONS

Jack A. Loeppky, Burke Gurney, Yoshio Kobayashi, Milton V. Icenogle, "Effects of ischemic training on leg exercise endurance", vol. 42, pp. 9-11 (Year: 2005).*
(Continued)

*Primary Examiner* — Tu A Vo
*Assistant Examiner* — Alexander Morales
(74) *Attorney, Agent, or Firm* — Jenkins, Wilson, Taylor & Hunt, P.A.

(57) ABSTRACT

An apparatus and method for ischemic muscle training or recovery provides coordinated blood flow restriction and electrical muscle stimulation. The apparatus includes a blood flow occluding element for restricting blood flow to a target muscle or muscle group in a user, and measuring resting systolic blood pressure (SBP). The apparatus also includes an electrical muscle stimulator including at least one electrode and a control unit which, upon activation, sends low amplitude electric pulses through the target muscle or muscle group forcing the targeted muscle to contract while the blood flow is restricted.

33 Claims, 10 Drawing Sheets

(51) Int. Cl.
    *A61N 1/36*     (2006.01)
    *A61B 17/135*   (2006.01)
    *A61B 5/1455*   (2006.01)
    *A61F 7/02*     (2006.01)
    *A61H 9/00*     (2006.01)

(52) U.S. Cl.
    CPC ........ *A61B 17/135* (2013.01); *A61B 17/1355* (2013.01); *A61F 7/02* (2013.01); *A61N 1/0476* (2013.01); *A61N 1/0484* (2013.01); *A61N 1/36003* (2013.01); *A61N 1/36031* (2017.08); *A61N 1/36034* (2017.08); *A61B 5/1455* (2013.01); *A61H 9/0092* (2013.01); *A61H 2201/02* (2013.01); *A61H 2201/10* (2013.01); *A61H 2201/165* (2013.01); *A61H 2205/106* (2013.01); *A61H 2230/208* (2013.01); *A61H 2230/30* (2013.01)

(58) Field of Classification Search
    CPC .......... A61H 2201/0103; A61B 5/0006; A61B 5/022; A61B 5/1455; A61B 5/14551; A61B 17/135; A61B 17/1355; A61B 5/0048; A61B 5/0053; A61B 5/02; A61B 5/0225; A61N 1/0452; A61N 1/0476; A61N 1/0484; A61N 1/36; A61N 1/36003; A61N 1/36014; A61F 7/02
    See application file for complete search history.

(56) References Cited

U.S. PATENT DOCUMENTS

| | | | | |
|---|---|---|---|---|
| RE40,863 | E * | 7/2009 | Tay | A61B 17/0057 606/50 |
| 8,287,474 | B1 * | 10/2012 | Koenig | A61F 5/41 601/148 |
| 8,361,107 | B2 * | 1/2013 | Graβl | A61N 1/0476 607/48 |
| 2002/0143365 | A1 * | 10/2002 | Herbst | A61N 1/0412 607/2 |
| 2003/0014088 | A1 * | 1/2003 | Fang | A61N 1/36003 607/48 |
| 2006/0058717 | A1 * | 3/2006 | Hui | A61H 9/0078 601/152 |
| 2007/0179585 | A1 * | 8/2007 | Chandler | A61N 1/0468 623/1.1 |
| 2009/0036938 | A1 * | 2/2009 | Shipley | A61N 1/36017 607/2 |
| 2009/0137884 | A1 | 5/2009 | Naghavi et al. | |
| 2009/0287243 | A1 | 11/2009 | Greennberg et al. | |
| 2010/0004715 | A1 * | 1/2010 | Fahey | A61N 1/0476 607/48 |
| 2010/0057149 | A1 * | 3/2010 | Fahey | A61H 11/00 607/3 |
| 2010/0105993 | A1 * | 4/2010 | Naghavi | A61B 5/411 600/301 |
| 2010/0211091 | A1 * | 8/2010 | Forsell | A61M 60/40 606/194 |
| 2010/0292619 | A1 * | 11/2010 | Redington | A61H 9/0078 601/84 |
| 2010/0324429 | A1 * | 12/2010 | Leschinsky | A61B 5/02208 600/493 |
| 2011/0125036 | A1 * | 5/2011 | Nakajima | A61F 5/34 600/500 |
| 2011/0251635 | A1 * | 10/2011 | Caldarone | A61B 17/132 606/202 |
| 2012/0238846 | A1 * | 9/2012 | Myers | A61B 5/022 600/324 |
| 2013/0296922 | A1 * | 11/2013 | Allen, IV | A61N 1/0412 607/2 |
| 2013/0304176 | A1 * | 11/2013 | Riddle | A61N 1/0456 607/149 |
| 2014/0031730 | A1 * | 1/2014 | Hornbach | A61B 5/4833 601/148 |
| 2014/0114117 | A1 | 4/2014 | Naghavi et al. | |

FOREIGN PATENT DOCUMENTS

WO    WO-2013025481 A  *  2/2013 .......... A61N 1/0484
WO    WO 2015/051457 A1   4/2015

OTHER PUBLICATIONS

Christopher M. Beaven, Christian J. Cook, Liam Kilduff, Scott Drawer, and Nicholas Gill, "Intermittent lower-limb occlusion enhances recovery after strenuous exercise", p. 1 (Year: 2012).*

Abe et al.: "*Effects of low-intensity cycle training with restricted leg blood flow on thigh muscle volume and VO2max in young men,*" Journal of Sports Science and Medicine, 2010, vol. 9 pp. 452-458.

Cole et al.: "*Response of the human triceps surae muscle to electrical stimulation during varying levels of blood flow restriction*" May 2000, published in European Journal of Applied Physiology, May 2000, vol. 82, Issue 1-2, pp. 39-44; available at: http://www.pubfacts.com/detail/10879441/Response-of-the-human-triceps-surae-muscle-to-electrical-stimulation-during-varving-levels-of-blood.

Inagaki et al.: "*Increase in serum growth hormone induced by electrical stimulation of muscle combined with blood flow restriction,*" Nov. 2011, published in European Journal of Applied Physiology, vol. III, Issue 11, pp. 2715-2721; available at: http://link.springer.com/article/10.1007%2Fs00421-011-1899-y Abstract.

Shang et al.: "*Noninvasive Optical Characterization of Muscle Blood Flow, Oxygenation, and Metabolism in Women With Fibromyalgia,*" Arthritis Res Ther. 2012;14(6), available at: http://www.medscape.com/viewarticle/804318 p. 1.

International Search Report for Application No. PCT/CA2014/050973 dated Dec. 16, 2014.

IPRP and Written Opinion for Application No. PCT/CA2014/050973 dated Apr. 12, 2016.

Examiner Requisition for Application No. 2926377 dated Nov. 18, 2020.

* cited by examiner

ISCHEMIC TRAINING APPARATUS AND METHOD

FIELD OF INVENTION

The present invention relates to an apparatus and method for restricting blood flow to a muscle and providing simultaneous electrical stimulation of the muscle to make it contract according to the training goals for the individual. The technology can be beneficially applied in exercise programs, physical training and recovery, and generally for other medical applications.

BACKGROUND OF THE INVENTION

The full benefits of physical activity or exercise are commonly unrealized. This can be true for elite athletes who exercise frequently, as well as for less active people who engage in exercise on a less frequent basis, or for persons with chronic disease, for whom exercise can be a great challenge.

People who exercise regularly can be susceptible to injury especially if they are exposed too soon to too great of an exercise stimulus, leading to "overtraining". Recovery from injury can interrupt a training schedule for a long time depending on the nature of the injury. Strength training, incorporated into a training schedule, can help reduce the risk of injury, but takes up time that could otherwise be used for more specific training requirements.

For athletes and more sedentary persons alike, one way to reduce the chance of overtraining and injury is to have a training schedule in which the level of exercise is increased slowly, starting with a low level of exercise and adding progressively greater demands. Injury can also be avoided by strengthening specific, often relatively underdeveloped, muscles.

Nonetheless, it is generally hard to predict injury and overtraining, which often manifests in immunosuppression or musculoskeletal injury, particularly about a joint. It can be difficult to know whether a given level of physical exercise is too much for the participant until the participant becomes injured, sick or suffers the effects of overtraining in other ways. Two effective methods of prevention are: 1) improved recovery between workouts, and 2) increased strength/fitness.

In acutely or chronically-diseased populations, the benefits of exercise are often not realized because the challenges of even light exercise are too great and the barriers to initiation too hard to overcome.

For clinical populations, there are clinical, community or home-based physical activity prescriptive programs and programs for rehabilitation. These programs typically have poor uptake. It is difficult for clinicians to control the amount of exercise undertaken by each patient, and there is often poor adherence by the patient to the prescription. The result can be that the patient is receiving an inappropriate dose of exercise, and is either not realizing the benefits of exercise or running the risk of injury or other adverse effect. Exercise programs can be resource-intensive and present barriers to delivery or uptake. When prescriptive, supervision is often necessary and specialized equipment may be required, all of which can be expensive. Under these programs, it can be difficult to target a particular muscle group without affecting related components of the musculoskeletal system. There are several technologies which have emerged to assist with athletic training or to aid generally in fitness and recovery.

For example, there are existing approaches that use electrical muscle stimulation to cause muscles to contract for the purpose of warming the muscle for rehabilitation, improving muscle firing or muscle rehabilitation itself. In theory, electric stimulators should be capable of causing muscle adaptive responses on par with typical exercise training; however, one reason for the ineffectiveness of this approach at inducing changes is the inability to sufficiently contract muscles without intense discomfort to the user owing to the required high intensity.

In other existing methods, passive exercise through electrical muscle stimulation has been combined with exercise, although the exercise is typically applied to the non-occluded limb and therefore not to the ischemic muscle wherein adaptation is magnified.

In other examples, occlusive technology has been combined with active exercise (such as riding a bike, using a treadmill, or lifting weights). Kaatsu training with specialized blood flow occluding bands is one example of this approach, and has become popular in many exercise regimes. The possible benefits of blood flow restricted exercise using low intensity traditional resistance or aerobic based exercise loads and manually restricted blood flow have been cited in the scientific literature. For example, Abe et al (Abe, T., Fujita, S., Nakajima, T., et al., Effects of low-intensity cycle training with restricted leg blood flow on thigh muscle volume and $VO_{2max}$ in young men, *Journal of Sports Science and Medicine*, 2010, vol. 9 pp. 452-458) found that low-intensity, short-duration, blood flow restricted exercise improved muscle hypertrophy and aerobic capacity in young men. Occlusive technology has not, however, been combined with passive exercise such as can be achieved through electrical muscle stimulation.

In other related applications, there are technologies that use compression garments or external counterpulsation devices (e.g. US2009/0287243 Greennberg et al.) which are designed to improve venous return to the heart. Such approaches are not designed to reduce blood flow or to combine blood flow restriction to a distal periphery with electrical muscle stimulation distal to the restriction. Instead, the timing of blood flow restriction associated with these types of approaches is designed to push blood back during diastole of the heart, and the length of blood restriction is prolonged to induce an ischemic cascade in musculature/vasculature below the level of occlusion. Such approaches do not target the skeletal muscle itself, nor are they intended to cause local physiological changes.

A further disadvantage of these and other existing approaches is that they do not support localized exercise training, and do not allow precise and specific training effects to be stimulated. Accordingly, there continues to be a need for new methods and technologies to enhance training effectiveness and overall fitness and recovery.

SUMMARY OF THE INVENTION

It is therefore an object of the invention to provide an improved system and method for ischemic muscle training or recovery.

According to an aspect of the invention, there is provided an ischemic muscle training or recovery apparatus which facilitates combined blood flow restriction and electrical muscle stimulation. The apparatus comprises:

a blood flow occluding element for restricting blood flow to a target muscle or muscle group in a user, and measuring resting systolic blood pressure (SBP); and an electrical muscle stimulator comprising at least one electrode and a control unit which, upon activation, is effective to send low amplitude electric pulses through the target muscle or muscle group forcing the targeted muscle to contract while the blood flow is restricted.

In certain non-limiting embodiments, a low amplitude electric pulse may include pulses of approximately 15-50 mA, or will otherwise involve the necessary intensity to evoke the individualized maximum tolerable contraction.

In a further non-limiting embodiment of the apparatus, the blood flow occluding element may be an occluding cuff adapted to inflate to a pressure causing either full or partial occlusion of blood flow for a period of approximately 0.5-20 min, while the electrical muscle stimulator activates forcing the targeted muscle to contract. The inflation of the occluding cuff may be accomplished using any type of fluid (i.e. gas, liquid) or by manual/automated constriction of a closed loop band.

In further embodiments, which are also non-limiting, the control unit may comprise an air pump, a circuit board and/or computer, integration timing components, and a power source. The control unit may also include a control panel with controls to adjust power to the apparatus, timing, duration and number of program cycles, pulse settings for electrical muscle stimulation, and/or occluding cuff intensity. In certain specific embodiments, which are not intended to be limiting, the occluding cuff may be an automated sphygmomanometer, with the control unit being connected to the sphygmomanometer by an air hose operably connected to the air pump, and electrical wiring as required to operate the sphygmomanometer. The control unit may also be configured for user-control of the frequency, duration and intensity of the electric pulses, or pre-programmed for automated control.

In other embodiments of the apparatus, the electrical muscle stimulator may comprise a plurality of pairs of electrodes adapted for attachment or placement directly in contact with the cutaneous surface of the user's limb above the target muscle. Alternately, the electrical muscle stimulator may comprise a plurality of pairs of electrodes in an intramuscular system adapted for stimulation of the target muscle. Without wishing to be limiting, it is also envisioned that the electrodes may be pre-arranged in pairs on sheets of material with adhesive for application to the skin, and with set distances between them on the sheet for specific muscle group placement.

In other optional embodiments, the apparatus may include a sensor to measure tissue oxygen saturation ($SmO_2$), e.g. using Near Infrared Spectroscopy (NIRS), and provide feedback to the blood flow occluding element and electrical muscle stimulator to facilitate pressure and timing parameters. In a non-limiting embodiment, the NIRS sensor may be configured to measure oxyhemoglobin saturation and adjust pressure based on a reduction of oxygen at the site of muscle stimulation.

The occluding cuff and at least one electrode may also be enclosed within a compression sleeve in further non-limiting embodiments. For example, the compression sleeve may be inflatable and adapted to apply a gradient of pressure which restricts blood flow by forcing blood from the target muscle or muscle group back toward the heart in the venous circulation.

In other optional embodiments, the apparatus may further include a heating and/or cooling element which can be used for localized heating and/or cooling of the target muscle or muscle group.

In a further aspect of the invention, there is also provided a method for ischemic muscle training or recovery by blood flow restriction and electrical muscle stimulation. The method comprises:

(a) measuring the blood pressure of the user and recording systolic and diastolic blood pressure peaks;

(b) occluding blood flow to a target muscle or muscle group in the user and maintaining the occlusion for a period of time;

(c) applying electrical muscle stimulation to one or more muscles or groups or muscles, distal to the site of blood flow occlusion, causing the one or more muscles or groups of muscles to contract while blood flow thereto is restricted;

(d) withdrawing the electrical muscle stimulation to the one or more muscles or groups of muscles and/or ceasing the occlusion of blood flow for a rest period; and (e) optionally repeating steps (b) through (d) for a determined number of cycles optimally effective for varying goals of muscle training and/or recovery. This may include, but is not limited to, targeting aerobic type muscular changes or muscle hypertrophy.

In certain non-limiting embodiments of the described method, the blood pressure of the user may be measured automatically or manually. Similarly, the systolic blood pressure and diastolic blood pressure peaks may be recorded automatically or by manually entering the values into a control unit.

In addition, the blood flow that is restricted may be an arterial blood flow, but can also be a venous blood flow by restricting venous return and causing blood congestion in the limb.

In further optional embodiments, the method may also include measuring tissue oxygen saturation ($SmO_2$), e.g. using a Near Infrared Spectroscopy (NIRS) sensor to provide feedback to the blood flow occlusion and muscle stimulation and facilitate pressure and timing parameters. For example, the NIRS sensor may be configured to measure oxyhemoglobin saturation and adjust pressure based on a reduction of oxygen at the site of muscle stimulation.

In specific examples of the method, the blood flow may be restricted in step (b) using an occluding cuff, by inflating the occluding cuff to a desired pressure. For example, yet without wishing to be limiting, the pressure used may be effective for complete occlusion of the blood flow, e.g. by inflating the occluding cuff to a pressure exceeding the systolic blood pressure, such as 130% or SBP, or within the range of 140-220 mmHg. The specific pressure is dependent on the blood pressure of the subject, and the size of the subject's limb, which in turn affect the width of the cuff used; as wider cuffs require higher pressures for occlusion. Approximate ranges may in specific examples include 160-220 mmHg with a wide cuff (10 cm), or 140-200 mmHg with a narrow cuff (5 cm). In other non-limiting examples, the pressure used may be effective for partial blood flow restriction, whereby the occluding cuff is inflated to a pressure value between the diastolic and systolic blood pressures. The pressure may be maintained, for example, for approximately 15 to 120 seconds before the electrical muscle stimulation is applied, more particularly about 60 seconds.

In addition, it is envisioned that the strength of muscle contraction resulting from the application of electrical muscle stimulation can either be controlled by the user, or automated.

Step (c) of the method, in non-limiting embodiments, may be carried out for a period of from about 1 to about 10 minutes. In other non-limiting embodiments, stimulation frequencies may range from 15 to 50 HZ and pulse durations from 250-400 microseconds. The rest period between trains may be from about 0.5 sec to about 5, and the number of cycles may range from about 10 to 100, with the possibility of repeating 1 to 10 iterations of a given program.

The electrical muscle stimulation may, in embodiments of the method, be applied in patterns which affect antagonistic muscles alternatively or simultaneously. In addition, the electrical muscle stimulation can be focused on a specific muscle group and all angles of attachment of the muscle, effective to cause an overloading stimulus to all segments of the muscle.

In particular examples of the method and apparatus, the user may be an athlete or military personnel, whereby the method and apparatus is used to reduce the incidence of overtraining and injury through carefully titrated exercise, or to supplement and increase recovery from workouts and resistance training. The user may also be one with an injury or recovering from a medical or surgical procedure, and whereby the apparatus and method is used to aid in recovery thereof. The user may also be a patient, for example, one with reduced mobility, whereby the apparatus and method is used for introducing exercise, and strengthening the patient's muscles or muscle groups.

BRIEF DESCRIPTION OF THE DRAWINGS

These and other features of the invention will become more apparent from the following description in which reference is made to the appended drawings wherein.

DETAILED DESCRIPTION

According to the present invention, blood flow to a particular muscle or muscle group is purposefully restricted, and the same muscle or muscle group is electrically stimulated. This approach allows controlled and localized training or treatment of particular muscles or muscle groups.

Blood flow restriction allows for significant muscular adaptations, using particularly low exercise loads. Thus by restricting blood flow, electrical muscle stimulation can thus be used at a tolerable level to evoke previously unattained/unreasonably painful results.

Thus, the invention relates to an ischemic muscle training apparatus which provides blood flow restriction and electrical muscle stimulation. In one embodiment, blood flow to a user's limb is restricted by an inflatable cuff, which measures the resting systolic blood pressure (SBP) and inflates to a pressure approximately between 140-240 mmHg (or up to a percentage of SBP e.g. for full occlusion 130% of SBP is commonly employed). The cuff can be placed at the proximal end of the user's limb. The cuff can, for example, range from three to 11 inches in width. In some embodiments of the apparatus, the cuff can be contained within a larger inflating sleeve, designed to apply a gradient of pressure (distal to proximal), restricting flow by forcing blood from the limb back toward the heart in the venous circulation. The increased venous return serves to decrease the chance of a detrimental ischemic cardiovascular event (heart attack) in chronically diseased or post-operative patients.

Pressure is maintained for a period of a few minutes while the electrical muscle stimulator activates, forcing the targeted muscle to contract. The electrical muscle stimulator functions by sending a low amplitude electric pulse through the muscle. The pulse is transferred from a control unit to the muscle by placing pairs of surface electrodes on the cutaneous surface above the target muscle. The pattern of firing (i.e. the frequency, duration and intensity of pulses) can be user-controlled according to the desired effects of training (for example whether it be more toward endurance type or strength/power type adaptations). In some embodiments, the system can be fully automated. In other embodiments, the pressure and electrical stimulation can be controlled manually or semi-manually by the user or an exercise therapist/health care provider.

For example, the system can be automated to track which muscles groups have been exercised at what time and for how long. This mechanism allows the system to ensure that workouts intended to induce strength training benefits are spaced appropriately (e.g. at least 72 hours apart), and only "recovery type" stimulation is applied to muscles between workouts.

The device can also track other sport specific workouts through user input and/or integration with other devices such as heart rate monitors or bicycle power meters to select an appropriate intensity of exercise or recovery.

Figure 1:
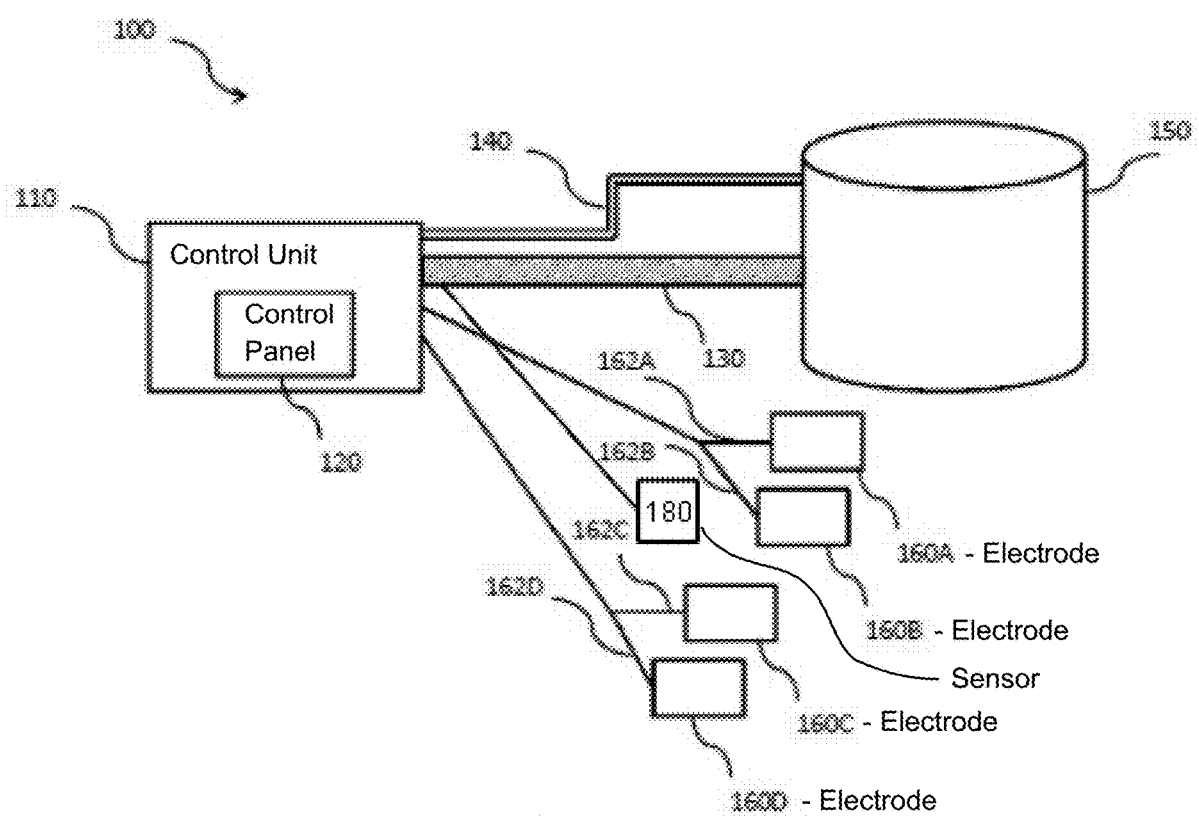
FIG. 1 shows an example of an embodiment of an ischemic training apparatus with an occluding cuff and electrodes for applying electrical muscle stimulation.

FIG. 1 shows an example of one non-limiting embodiment of an ischemic training apparatus 100 with an occluding cuff 150 and electrodes 160A-D for applying electrical muscle stimulation. Apparatus 100 further comprises control unit 110, control panel 120, air hose 130, electrical wiring 140, and electrical wiring 162A-D to electrodes 160A-D.

Control unit 110 comprises an air pump, a circuit board and/or computer, integration timing components, and a battery or other suitable power source.

Control panel 120 on control unit 110 comprises control switches such as for example an on/off switch and an emergency off switch. Control panel 120 also comprises devices for adjusting control parameters which can include for example timing, duration and number of program cycles, pulse settings for electrical muscle stimulation, and occluding cuff intensity control.

Control unit 110 is connected to occluding cuff 150 by air hose 130 and electrical wiring 140. Occluding cuff 150 is inflated via air hose 130 using air from an air pump (not shown) housed in the control unit 110. When occluding cuff 150 is inflated, blood flow to muscle distal to cuff 150 is restricted to a degree determined by the level of inflation of cuff 150.

In the embodiment shown in FIG. 1, electrical wiring 140 connects control unit 110 to cuff 150, as required for an automated sphygmomanometer (blood pressure cuff).

In one embodiment (shown in FIG. 1), electrodes 160A through 160D are connected to control unit 100 by electrical wiring 162A-D. Any number of pairs of electrodes may be used. Electrodes 160A-D are attached to the skin of the user or patient and located to provide electrical muscle stimulation of the desired muscles or muscle groups. Control unit 110 comprises equipment to provide electrical muscle stimulation to the muscles via electrical wiring 162A-D and electrodes 160A-D.

In operation, apparatus 100 inflates cuff 150 to restrict blood flow distal to cuff 150, and applies electrical muscle stimulation to muscles distal to cuff 150 via electrical wiring 162A-D and electrodes 160A-D.

In an optional embodiment, the apparatus 100 may further include a sensor 180 to measure tissue oxygen saturation ($SmO_2$) and provide feedback to the blood flow occluding element and electrical muscle stimulator, and facilitate pressure and timing parameters. For example, the sensor 100 may be a Near Infrared Spectroscopy (NIRS) sensor, and be configured within the system to measure oxyhemoglobin saturation and adjust pressure based on a reduction of oxygen at the site of muscle stimulation.

Figure 1A:
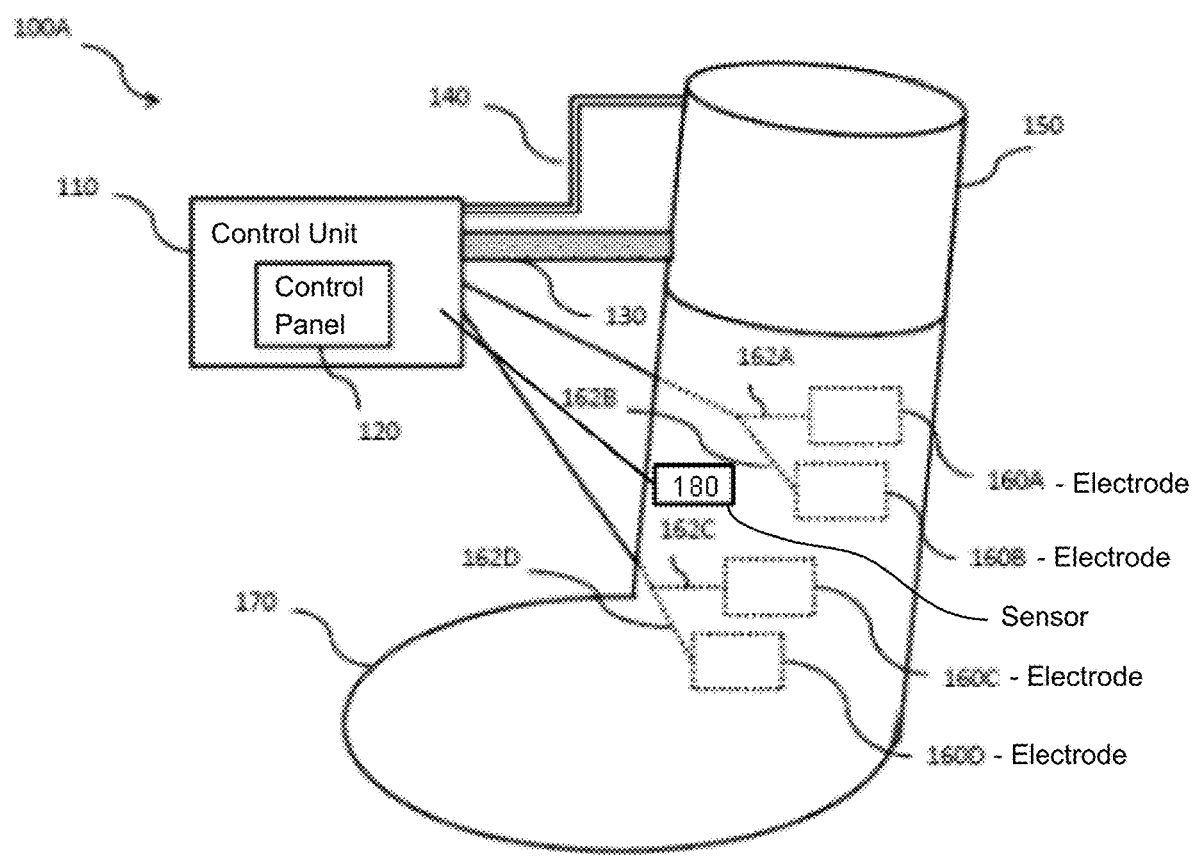
FIG. 1A shows an example of an embodiment of an ischemic training apparatus with a cuff and electrodes for applying electrical muscle stimulation enclosed in a sleeve.

FIG. 1A shows a further example of a non-limiting embodiment of an ischemic training apparatus 100A, with a cuff 150 and electrodes 160A-D (for applying electrical muscle stimulation) enclosed in a sleeve 170. In some embodiments, sleeve 170 is a compression sleeve. For example, sleeve 170 can be inflatable to provide full limb compression. In other embodiments, sleeve 170 does not provide additional compression, but serves as a convenient way of placing electrodes on the user. Electrodes 160A-D can be inside sleeve 170 as indicated by the dotted lines in FIG. 1A. Other components of apparatus 100A and its operation are as described for FIG. 1.

In other embodiments, blood flow can be controlled by changing the pressure around the entire body, a portion of the body or a single limb using air, water or other fluids (e.g. in a hypo- or hyperbaric chamber). After applying this pressure to the desired area for the purposes of changing blood flow, electrical muscle stimulation can be applied to introduce an exercise stimulus of the desired intensity.

Figure 2:
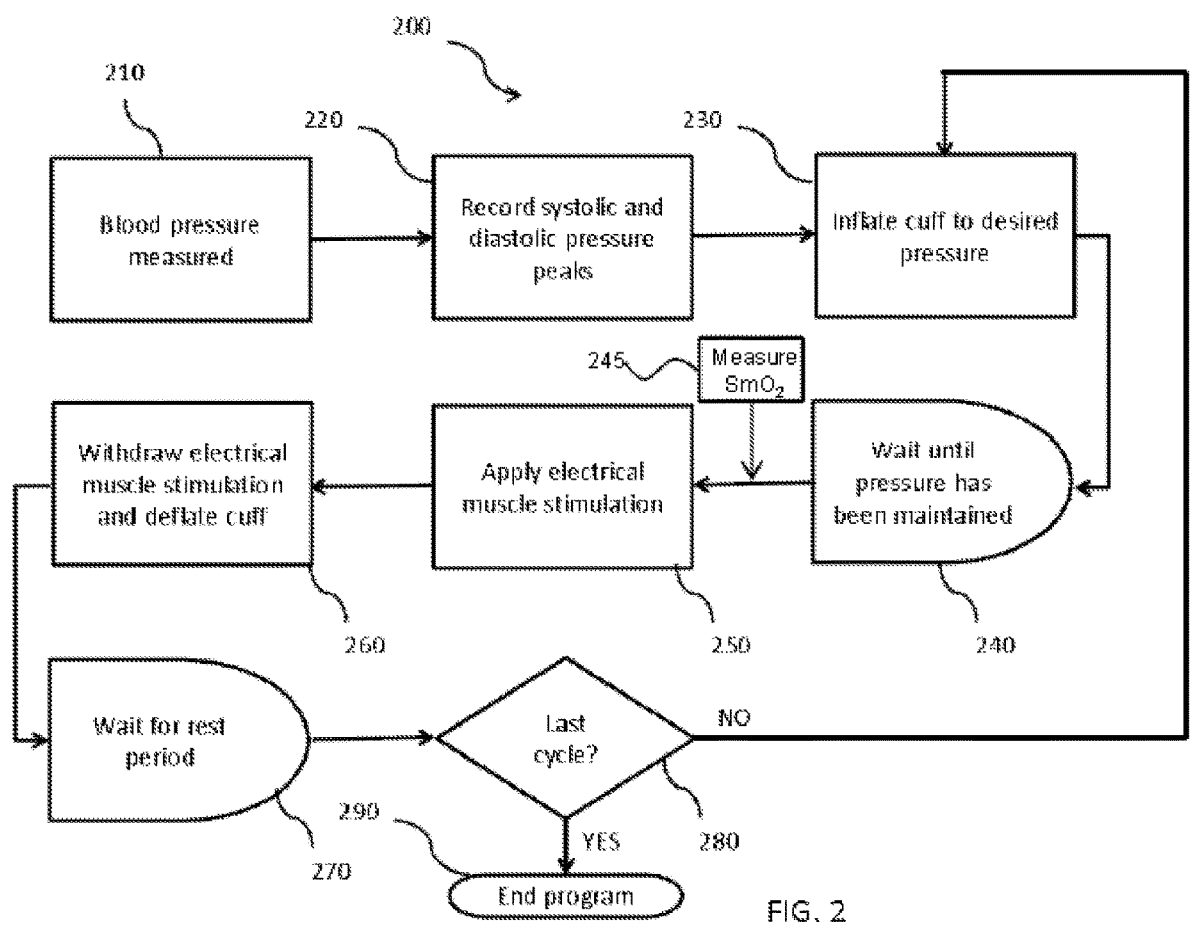
FIG. 2 shows an example of a method for operating an ischemic training apparatus.

FIG. 2 shows an example of a non-limiting embodiment of a method for operating an ischemic training apparatus. For example, method 200 can be used to operate apparatus 100 from FIG. 1 or other embodiments of the present technology. Method 200 can be implemented by manual or automatic means.

Method 200 begins at step 210 where the blood pressure of the user or patient is measured. In some embodiments, the measurement of blood pressure can be done automatically. In other embodiments, the measurement of blood pressure can be done manually. Method 200 then proceeds to step 220 where apparatus 100 records the systolic blood pressure and diastolic blood pressure peaks by automatic means or by a human operator entering the values into control unit 110 from FIG. 1.

Method 200 proceeds next to step 230 and cuff 150 from FIG. 1 is inflated to a desired pressure. The desired pressure is determined by the required occlusion level which in turn is dependent on the pre-existing conditions and exercise training goals of the user or patient. For example, if complete occlusion is desired, cuff 150 can be inflated to a pressure exceeding the systolic blood pressure (for example 130% of SBP or 140-220 mmHg). In other examples, where complete occlusion is not desired, then cuff 150 is inflated to a pressure value between the diastolic and systolic blood pressures, resulting in partial blood flow restriction.

At step 240, the pressure is maintained for a short period of time (e.g. 30-60 seconds) after which method 200 proceeds to step 250 and electrical muscle stimulation is applied. Electrical muscle stimulation can be applied to one or more selected muscles or groups of muscles, causing the muscles to contract. To achieve the benefits of blood flow restriction, electrical muscle stimulation is applied to muscles distal to the occlusion site. For example, if cuff 150 from FIG. 1 is placed around the thigh, electrical muscle stimulation can be applied to the hamstring or calf muscle.

In some embodiments, the strength of the muscle contraction resulting from applying electrical muscle stimulation at step 250 can be controlled by the user through the mechanisms provided, for example on control panel 120 from FIG. 1. Similarly, parameters of contraction length, intensity, pulse frequency or any other relevant parameter can be controlled and selected according to the goals of the exercise program. In some embodiments, automated programs can be pre-programmed into apparatus 100. In other embodiments, the control can be provided manually.

In another optional embodiment, a step 245 may be carried out whereby tissue oxygen saturation ($SmO_2$) is measured to provide feedback to the blood flow occlusion and muscle stimulation and facilitate pressure and timing parameters. This can be carried out, for example, using a Near Infrared Spectroscopy (NIRS) sensor configured to measure oxyhemoglobin saturation and adjust pressure based on a reduction of oxygen at the site of muscle stimulation.

At step 260, following a period of occlusion with electrical stimulation, the electrical stimulus is withdrawn and the blood occlusion-ceased by deflating cuff 150. The period of restriction may for example be a few minutes, and at step 270 is followed by a rest period. The rest period may be pre-determined or selectable. At the end of the rest period, method 200 proceeds to step 280. If the present cycle is the last cycle in the exercise program (YES), then method 200 proceeds to step 290 and the program ends. If the present cycle is not the last cycle in the exercise program (NO), then method 200 proceeds to step 230 and the cycle begins again.

In some embodiments, the length of the rest period may be determined by the exercise training goals of the specific program selected. In some embodiments, electrical muscle stimulation may be applied without blood flow restriction during the rest period. In other embodiments blood flow restriction may be applied without stimulation as part of the work/rest/recovery cycle.

In some embodiments, the apparatus can incorporate local heating or cooling of the muscle(s). The addition of a heat/cold modality may be beneficial in altering blood flow of the more superficial tissue. For example, vasodilation may add to the re-perfusion effect of blood re-entering the area after the occlusion has been withdrawn.

In some embodiments, the pairs of electrodes required for electrical muscle stimulation can be placed manually in the appropriate places on skin adjacent to the targeted muscles. In other embodiments, the electrodes can be pre-arranged on sheets of material which are applied to the skin, and can cover multiple muscles and be activated by the control unit according to an exercise program. In some embodiments, the electrodes can come in matched pairs with set distances between them on the sheet (for specific muscle group placement). The apparatus can sense and select which pairs to fire or whether to fire in individual pairings. For sheet placement, lines for orientation on the body can be printed and the computer in the control unit can track which pairs best align with the underlying muscles for maximal contraction.

Electrodes can be activated in patterns which affect antagonistic muscles alternatively (i.e. first the extensors around a joint and then the flexors). This approach provides a more time-efficient and balanced workout. Balance is also important to avoiding injury.

Electrodes can also be activated so as to focus on specific muscles groups and all angles of attachment of the muscle to ensure an "overloading stimulus" affecting all segments of the muscle.

Firing electrodes of antagonistic muscles simultaneously can also offer a time-efficient option by exercising muscles intended to flex and extend joints at the same time (and potentially allowing strong isometric contractions without joint flexion or extension).

In some embodiments, a motion sensor can be used to detect the effect of electrical muscle stimulation on a muscle for a given stimulus, and can be used to provide feedback to adjust the timing and strength of stimulation. Any other suitable biofeedback mechanism such as impedance, ultrasound, or near-infrared spectroscopy measurements can also be used to control the timing and strength of stimulus.

For athletes, the above described technology can reduce the likelihood of overtraining and injury through exercise, primarily through controlling the "off-field" stimulus as opposed to that imposed during regular workouts. The technology provides a controlled and targeted training of particular muscles under beneficial ischemic conditions. The above described technology may also be beneficial for supplementing and recovering from sport-specific workouts and resistance training sessions, allowing better training to occur. In the case of injury, the above described technology can speed recovery through a controlled program of exercise that increases in intensity in an appropriate fashion. This specific use would be akin to (and perhaps in place of) cool down exercises traditionally performed by running, riding a stationary bike or stretching. Similarly, in clinical situations, the above described technology provides a controlled program for introducing exercise and increasing its intensity while reducing the likelihood of injury or harm. The above described technology may be particularly beneficial for introducing exercise to immobile patients, and for recovery from acute or chronic conditions.

In addition to training, exercise and injury recovery for humans, the technology has potential applications for animals including veterinary science and dog/horse racing.

EXAMPLE 1

Blood Flow Restriction and Muscle Stimulation to Stimulate Alterations in Strength and Hypertrophy Effects of blood flow restriction and electrical muscle stimulation for increasing strength and muscle size in humans was determined. The combined stimulus of blood flow restriction and electrical muscle stimulation was compared with each stimulus alone. Participants were assigned to one of four of the conditions detailed below, allowing direct comparisons. Participants trained using the indicated stimulus 4 d/wk, for 32 min each session for a period of 6 weeks. For all conditions including electrical stimulation, the stimulator was used at the highest intensity the participant could tolerate for the duration of the training session. Blood flow occlusion was performed intermittently 4 min on, 4 min off.

Participant leg strength was tested at baseline, and then participants were randomly assigned to 6 weeks of training according to one of the following four conditions: 1) control; 2) electrical stimulation only (TEMS); 3) blood flow restriction only (BFR); or 4) combined blood flow restriction and electrical stimulation (BFR+TEMS), Mean delta scores for measures of muscular strength, muscular endurance and muscular size following training are presented in FIGS. 3A, 3B, 4, 5A, 5B, 6A, and 6B, and Tables 1-6.

TABLE 1

Mean isometric leg strength following 6 weeks of training under different conditions.

| CONDITION | LEG STRENGTH |
|---|---|
| BFR Only | 15.847 |
| TEMS Only | 18.404 |
| BFR + TEMS | 31.224 |
| Control | 4.383333333 |

TABLE 2

Differences in isometric leg strength by group-significance, $p = 0.05$
Difference by group- significance $p = 0.05$
Leg strength (post Hoc)

| Group | VS | Mean Diff | St. Error | p value |
|---|---|---|---|---|
| control | BFR | −11.4637 | 9.26584 | .224 |
|  | TEMS | −14.0207 | 9.26584 | .139 |
|  | BFR + TEMs | −26.8407* | 9.26584 | .006 |

Figure 3A:
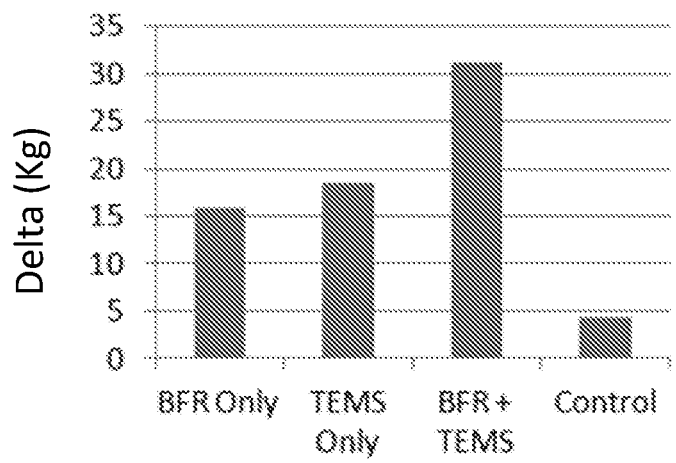
FIGS. 3A and 3B show an example of increases in isometric leg strength following 6 weeks of training under different conditions.
Figure 3B:
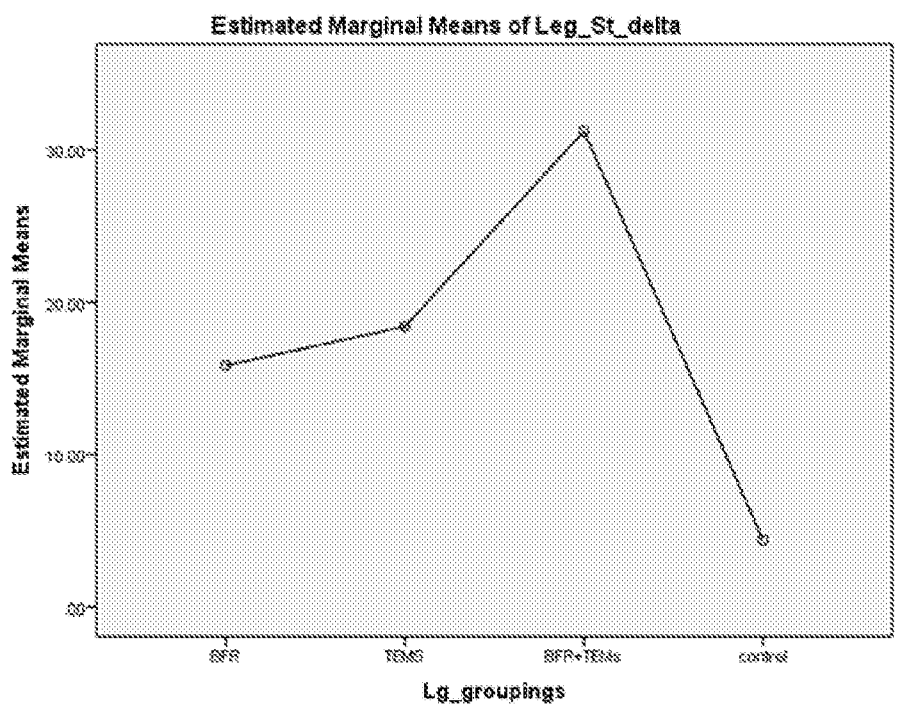

The data shown in TABLE 1 is graphically represented in FIGS. 3A and 3B.

As shown in FIGS. 3A and 3B, and Tables 1 and 2, isometric leg strength increased above the baseline levels following 6 weeks of training. Only the combined group, BFR+TEMs, showed statistically significant differences from the control group. These results indicate that the combination of blood flow restriction with electrical muscle stimulation confers additional benefit compared to either modality alone for causing alteration in leg strength.

TABLE 3

Mean leg muscular endurance following 6 weeks of training under different conditions.

| CONDITION | Muscular Endurance |
|---|---|
| BFR Only | 13.516 |
| TEMS Only | 14.741 |
| BFR + TEMS | 22.99911111 |
| Control | 14.12833333 |

Figure 4:
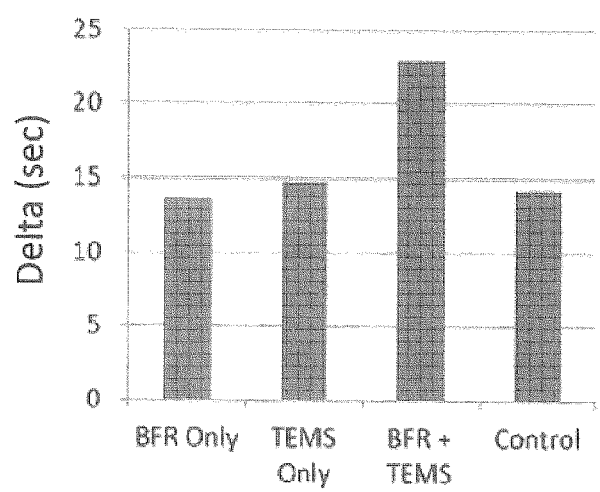
FIG. 4 shows an example of increases in isometric leg endurance following 6 weeks of training under different conditions.

The data shown in TABLE 3 is graphically represented in FIG. 4.

As shown in TABLE 3 and FIG. 4, muscular endurance increased above baseline in all groups, suggesting that another factor (e.g. learning how to do the test better) may have had an influence. Most groups increased similarly to control, whereas the combined (BFR+TEMs) group had a greater response. Indeed, muscular endurance increased to a greater extent in the combined group than any other group.

TABLE 4

Mean muscle girth following 6 weeks of training under different conditions.

| CONDITION | Muscle Girth |
|---|---|
| BFR Only | 0.01 |
| TEMS Only | 1.1946 |
| BFR + TEMS | 1.9866 |
| Control | −0.7 |

TABLE 5

Differences in muscle girth by group-significance, p = 0.06.
Difference by group- significance p = 0.006
Leg girth (post hoc)

| Group | VS | Mean Diff | St. Error | p value |
|---|---|---|---|---|
| control | BFR | −.7100 | .77241 | .838 |
| | TEMS | −1.8946 | .77241 | .131 |
| | BFR + TEMs | −2.6866* | .77241 | .015 |

Figure 5A:
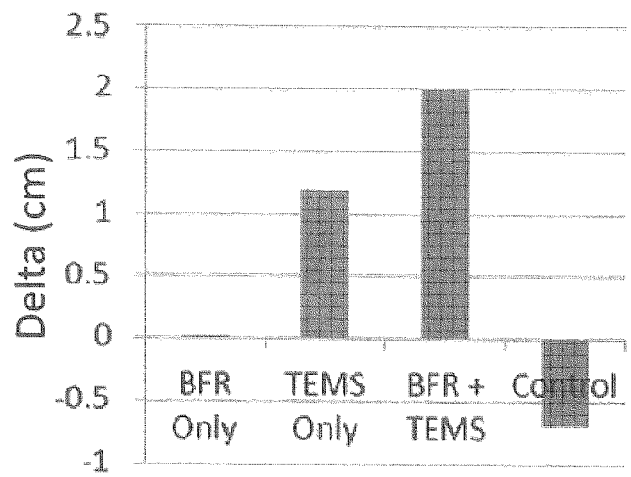
FIGS. 5A and 5B show an example of differences in muscle girth following 6 weeks of training under different conditions.
Figure 5B:
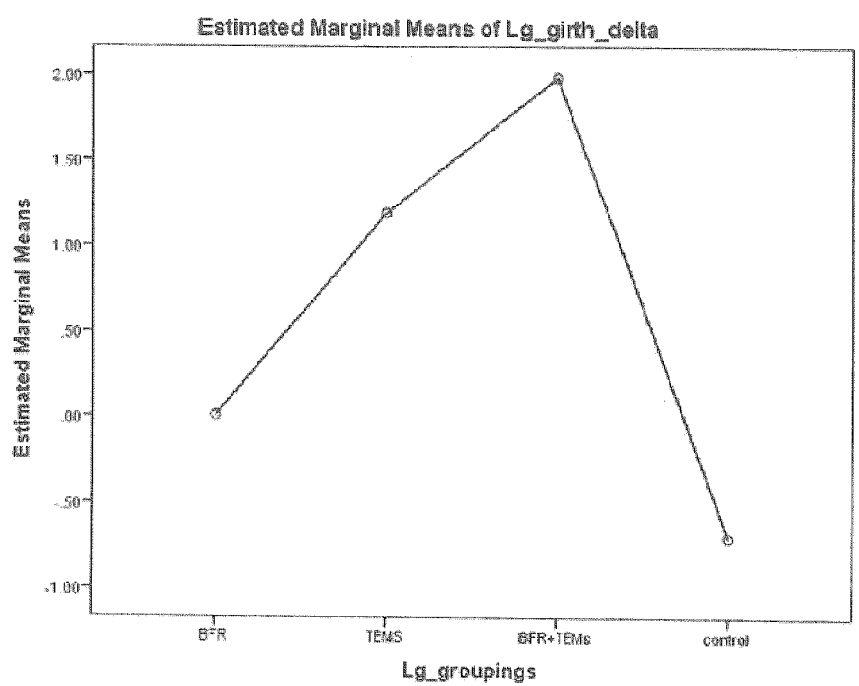

The data shown in Table 4 is graphically represented in FIGS. 5A and 5B.

As shown in FIGS. 5A and 5B, and Tables 4 and 5, muscle girth, indicative of alterations in muscle size, were the greatest in the combined (BFR+TEMs) group. Alterations in muscle girth were not statistically different from the control in any group except the combined group. These results support the literature which shows that TEMS alone is relatively ineffective at causing hypertrophy (attributed to the intensity of contraction required). When combined with blood flow restriction, TEMS is more effective—in agreement with the effect in the reported literature for traditional exercise training with blood flow restriction, which has shown that when training (dynamic weight lifting) using occlusion methods, alterations in strength and hypertrophy can occur with loads that are 20-30% of max (vs. the 70-80% required without occlusion).

TABLE 6

Differences in muscle cross-sectional area.
DEXA (post hoc)

| Group | VS | Mean Diff | St. Error | p value |
|---|---|---|---|---|
| control | BFR | −309.7333* | 144.61196 | .039 |
| | TEMS | −284.7333 | 144.61196 | .057 |
| | BFR + TEMs | −301.1333* | 144.61196 | .045 |

Figure 6A:
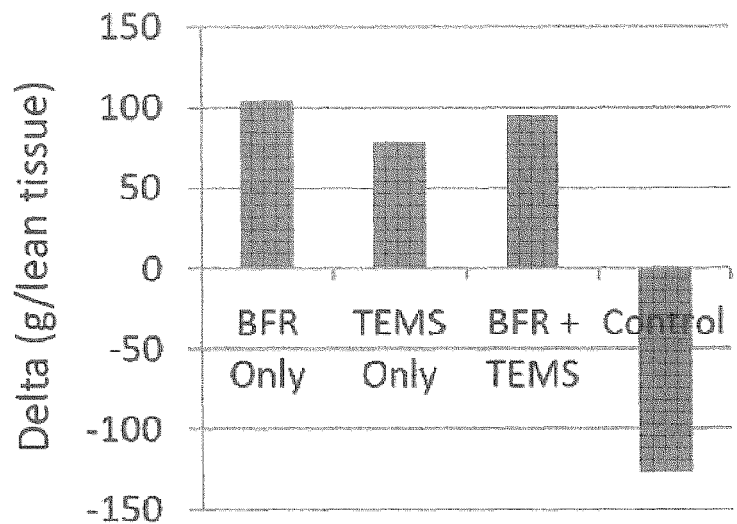
FIGS. 6A and 6B show an example of differences in muscle cross-sectional area following 6 weeks of training under different conditions.
Figure 6B:
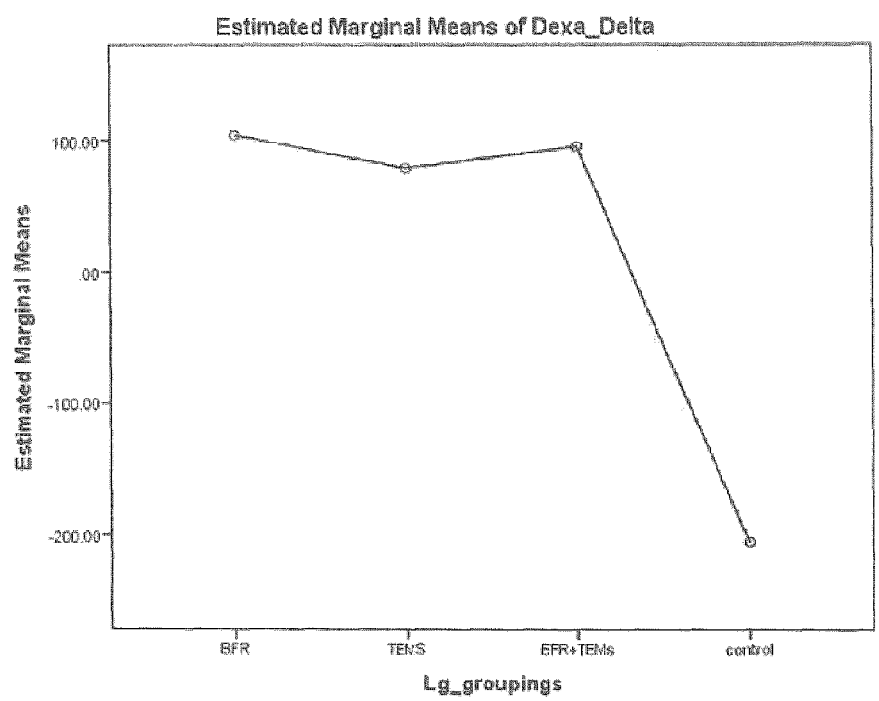

The data shown in Table 6 is graphically represented in FIGS. 6A and 6B.

As shown in FIGS. 6A and 6B, and Table 6, muscle cross-sectional area increased above baseline following 6 weeks of training. Alterations in muscle cross-sectional area was measured by dual x-ray absorptiometry (DEXA). The data objectively confirms the findings for leg girth described above.

The results of these studies are applicable to applications in rehab (orthopedic, cardiovascular, other surgeries, bedrest, chronic disease (diabetes)). This may also have applications to athletic populations.

EXAMPLE 2

Recovery and Post-Recovery Performance Following Extremely Taxing Exercise

Experiments were performed to understand if using a combination of blood flow restriction and electrical muscle stimulation was more effective for stimulating muscular recovery (and repeated exercise performance) than doing nothing at all, or employing either modality in isolation. The subjective feelings of leg pain experienced by subjects as a result of exposure to a 40 min session of downhill running (60% of $VO_2$ max, −12° decline), which accentuates the eccentric muscular contractions that occur with each step, was also tracked.

Participants (n=20) performed a 10 km simulated time trial on a cycle ergometer within the lab. Following this, participants were exposed to fatigue (and muscle soreness) inducing exercise, in the form of downhill running and then randomized to one of four conditions: 1) control; 2) electrical stimulation only (TEMS); 3) blood flow restriction only (FFR); or 4) combined blood flow restriction and electrical stimulation (BFR+TEMS). Participants used this mode of recovery immediately following the exercise, during one day of no exercise and then preceding the repeated 10 km time trial. Difference scores between the pre- and post average speeds maintained throughout the trials are presented in FIG. 7, with both pre and post ride times presented in FIG. 8.

Figure 7:
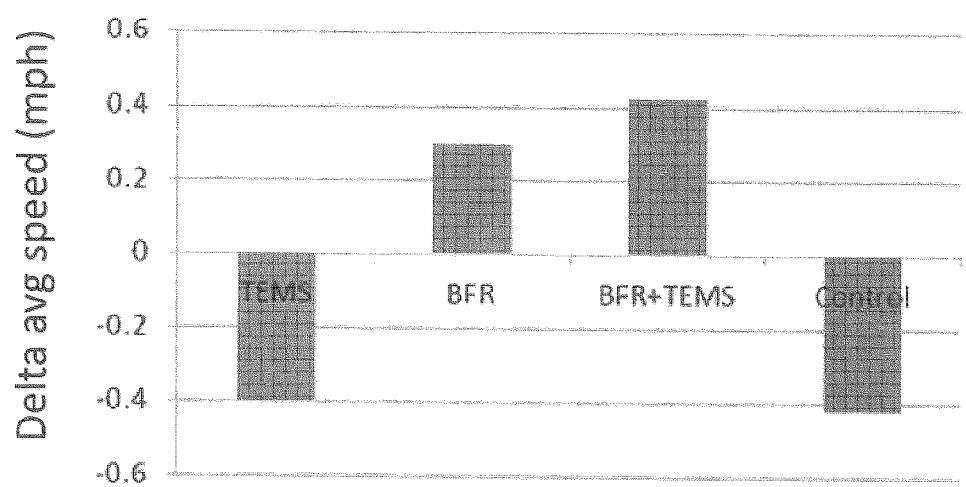
FIG. 7 shows an example of differences in average speed (mph) from a first ride to a second ride following muscle soreness inducing exercise, where different recovery techniques were used.
Figure 8:
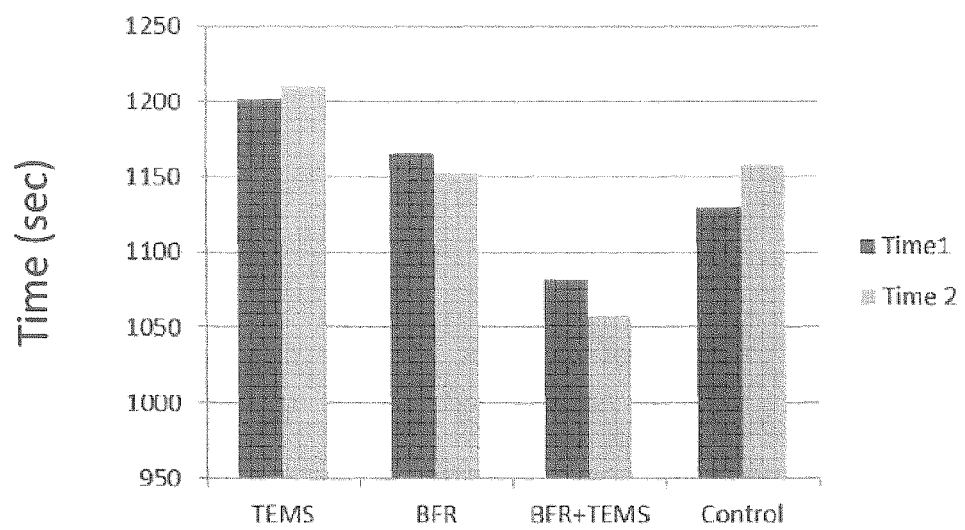
FIG. 8 shows an example of differences in amount of time (sec) required to complete a 10 km time trial pre and post treatment under different conditions.

As shown in FIGS. 7 and 8, participants using BFR and BFR+TEMs had a greater recovery than those who used TEMs alone or did not use a recovery technique (control). A decrease in performance is the expected response, however the use of BFR led to an increase in performance and a greater increase when combined with TEMs. FIG. 7 shows the difference in average speed (mph) from ride 1 to ride 2 following muscle soreness inducing exercise. FIG. 8 shows the amount of time (sec) required to complete the 10 km time trial, pre (dark grey) and post (light grey), therefore lower values equate to better performance.

These results indicate that the use of BFR+TEMs could be the most effective technique of muscle recovery studied, above the effects of BFR alone, and certainly more so than TEMs or control. Of note, the BFR+TEMs group represented the most elite riders (by chance through random allocation), evident in the fastest pre 10 km time. This group would thus be expected to have the least variation in performance owing to external influences, such as poor pacing, etc. Importantly, it was also this group who saw the greatest improvements in time/pace.

TABLE 7

Differences in perception of increased leg pain at 48 hr by group.

| Group | Vs | Mean diff | St Error | P value |
|---|---|---|---|---|
| Control | TEMS | −0.68 | 1.20451 | 0.581 |
| | BFR | 1.8333 | 1.15904 | 0.135 |
| | BRF_TEMS | 2.7 | 1.26966 | 0.05 |

Figure 9:
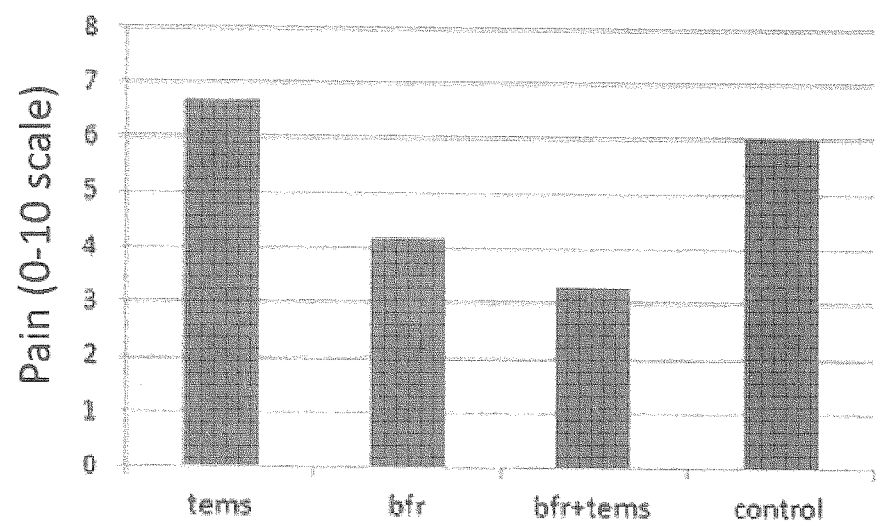
FIG. 9 shows differences in perception of increased leg pain at 48 hr following exercise, using different conditions.

The data shown in TABLE 7 is graphically represented in FIG. 9.

As shown, when compared with baseline values, there were differences in perception of increased pain at 48 hr by group (p=0.042). Participant's subjective rating of pain (in a 10 cm analogue scale) was significantly lower at 48 hr in the BRF+TEMs group.

Exposure to intense eccentric exercise is expected to cause delayed onset muscle soreness, which typically peaks at 48 hr post exposure. The use of combined blood flow restriction and TEMs blunted the perceived increase in pain at 48 hr, and could well be related to the improved performance of this group.

The results of these studies are primarily applicable to athletic/human performance applications.

One or more currently preferred embodiments have been described by way of example. It will be apparent to persons skilled in the art that a number of variations and modifications can be made without departing from the scope of the invention as defined in the claims.

What is claimed is:

1. An ischemic muscle training or recovery apparatus for simultaneous blood flow restriction and electrical muscle stimulation, comprising:
    a blood flow occluding element for restricting blood flow to a target muscle or muscle group in a user distal to the blood flow occluding element, and measuring resting systolic blood pressure (SBP), wherein the blood flow occluding element is configured to surround a proximal end of a user's limb above the target muscle or muscle group;
    an electrical muscle stimulator comprising at least one electrode and a control unit which, upon activation, is effective to send low amplitude electric pulses through the target muscle or muscle group forcing the target muscle or muscle group to contract while the blood flow is restricted, wherein the at least one electrode is adapted for placement directly in contact with a cutaneous surface of the user's limb above the target muscle or muscle group; and
    a sensor for measuring tissue oxygen saturation (SmO2) configured to provide feedback to the blood flow occluding element and the electrical muscle stimulator to facilitate pressure and timing parameters of the blood flow occluding element and to adjust timing parameters of stimulation by the electrical muscle stimulator.

2. The apparatus of claim 1, wherein the blood flow occluding element is an occluding cuff adapted to inflate to a pressure causing either full or partial occlusion of blood flow for a period of about 0.5-20 min, while the electrical muscle stimulator activates forcing the targeted muscle to contract.

3. The apparatus of claim 2, wherein the control unit comprises an air pump, a circuit board and/or computer, integration timing components, and a power source.

4. The apparatus of claim 3, wherein the control unit further comprises a control panel with controls to adjust power to the apparatus, timing, duration and number of program cycles, pulse settings for electrical muscle stimulation, and/or occluding cuff intensity.

5. The apparatus of claim 3, wherein the occluding cuff is an automated sphygmomanometer, and the control unit is connected to the sphygmomanometer by an air hose operably connected to the air pump, and electrical wiring configured to operate the sphygmomanometer.

6. The apparatus of claim 2, wherein the occluding cuff and the at least one electrode are enclosed in a compression sleeve.

7. The apparatus of claim 6, wherein the compression sleeve is inflatable and adapted to apply a gradient of pressure which restricts blood flow by forcing blood from the target muscle or muscle group back toward the heart in the venous circulation.

8. The apparatus of claim 1, wherein the at least one electrode of the electrical muscle stimulator comprises a plurality of pairs of electrodes.

9. The apparatus of claim 1, wherein the at least one electrode of the electrical muscle stimulator comprises a plurality of pairs of electrodes adapted for implantation for stimulation of the target muscle.

10. The apparatus of claim 1, wherein the control unit is adapted for user-control of the frequency, duration and intensity of the electric pulses, or pre-programmed for automated control of the frequency, duration and intensity of the electric pulses.

11. The apparatus of claim 1, wherein the electrodes are pre-arranged in pairs on sheets of material with adhesive for application to the skin, and with set distances between them on the sheets for specific muscle group placement.

12. The apparatus of claim 1, wherein the sensor for measuring tissue oxygen saturation (SmO2) comprises a Near Infrared Spectroscopy (NIRS) sensor to provide the feedback to the blood flow occluding element and the electrical muscle stimulator.

13. The apparatus of claim 12, wherein the NIRS sensor is configured to measure oxyhemoglobin saturation and adjust pressure based on a reduction of oxygen at the target muscle or muscle group.

14. A method for ischemic muscle training or recovery by simultaneous blood flow restriction and electrical muscle stimulation, comprising:
    (a) measuring a blood pressure of the user and recording systolic and diastolic blood pressure peaks;
    (b) occluding blood flow to a target muscle or muscle group in the user and maintaining a blood flow occlusion for a period of time, wherein blood flow is restricted by placing a blood flow occluding element around a proximal end of a user's limb of the user above the target muscle or muscle group that is distal to the blood flow occluding element;
    (c) applying electrical muscle stimulation to one or more muscles or groups of muscles, distal to a site of blood flow occlusion, causing the one or more muscles or groups of muscles to contract while blood flow thereto is restricted, wherein the application of electrical muscle stimulation includes attaching or placing at least one electrode directly in contact with a cutaneous surface of the user's limb above the target muscle or muscle group;
    (d) positioning a sensor for measuring tissue oxygen saturation (SmO2) to provide feedback to the blood flow occlusion, to facilitate pressure and timing parameters of the blood flow occlusion, and to adjust timing parameters of the electrical muscle stimulation; and
    (e) withdrawing the electrical muscle stimulation to the one or more muscles or groups of muscles and/or ceasing the blood flow occlusion for a rest period; and
    wherein steps (b) through (e) are carried out for a determined number of cycles.

15. The method of claim 14, wherein the blood pressure of the user is measured automatically or manually.

16. The method of claim 14, wherein values of the systolic blood pressure and diastolic blood pressure peaks are recorded automatically or by entering the values into a control unit.

17. The method of claim 14, wherein the sensor for measuring tissue oxygen saturation (SmO2) comprises a Near Infrared Spectroscopy (NIRS) sensor to provide the feedback to the blood flow occlusion and muscle stimulation.

18. The method of claim 17, wherein the NIRS sensor is configured to measure oxyhemoglobin saturation and adjust pressure based on a reduction of oxygen at the target muscle or muscle group.

19. The method of claim 14, wherein the blood flow occluding element comprises an occluding cuff, and the occluding cuff is inflated to a desired pressure.

20. The method of claim 19, wherein the desired pressure is effective for complete occlusion of the blood flow, and the desired pressure exceeds the systolic blood pressure.

21. The method of claim 20, wherein the occluding cuff is inflated to between 140-220 mmHg.

22. The method of claim 19, wherein the pressure is effective for partial blood flow restriction, and the pressure is at a pressure value between the diastolic and systolic blood pressures.

23. The method of claim 19, wherein the pressure is maintained for about 15 to 120 seconds before the electrical muscle stimulation is applied.

24. The method of claim 14, wherein the application of electrical muscle stimulation is controlled by the user, or is automated.

25. The method of claim 14, wherein step (c) is carried out for a period of from 1 to 10 minutes.

26. The method of claim 14, wherein the rest period of step (e) is carried out for a period of from 0.5 to 5 seconds.

27. The method of claim 14, wherein the number of cycles ranges from 1 to 100, and a program of cycles is repeated up to 10 times.

28. The method of claim 14, wherein the electrical muscle stimulation is applied in patterns which affect antagonistic muscles alternatively or simultaneously.

29. The method of claim 14, wherein the electrical muscle stimulation is focused on a specific muscle group, effective to cause an overloading stimulus to all segments of the muscle.

30. The method of claim 14, wherein the ischemic muscle training or recovery method reduces an incidence of overtraining and injury through exercise.

31. The method of claim 14, wherein the ischemic muscle training or recovery method aids recovery from sport-specific workouts and resistance training.

32. The method of claim 14, wherein the user has an injury, and the ischemic muscle training or recovery method aids recovery from the injury.

33. The method of claim 14, wherein the user is a patient with reduced mobility, and the ischemic muscle training or recovery method is used for introducing exercise and strengthening the patient's muscles or muscle groups.

* * * * *